United States Patent [19]

Manoury et al.

[11] 4,406,907
[45] Sep. 27, 1983

[54] CERTAIN 2,5-DISUBSTITUTED PYRIDINE DERIVATIVES PRODUCING β-ADRENERGIC BLOCKING ACTION

[75] Inventors: Philippe Manoury, le Plessis Robinson; Jean Binet, Breuillet; Icilio Cavero, Creteil, all of France

[73] Assignee: Synthelabo, Paris, France

[21] Appl. No.: 361,200

[22] Filed: Mar. 24, 1982

[30] Foreign Application Priority Data

Mar. 25, 1981 [FR] France ................. 81 06005

[51] Int. Cl.³ .............. A61K 31/44; C07D 213/69
[52] U.S. Cl. ................................ 424/263; 546/296
[58] Field of Search ................... 546/296; 424/263

[56] References Cited

U.S. PATENT DOCUMENTS 4,115,575 9/1978 Frei et al. ................. 424/250
4,195,090 3/1980 Frei et al. ................. 424/263

FOREIGN PATENT DOCUMENTS 2218101 9/1974 France ................. 424/250

Primary Examiner—Alan L. Rotman
Attorney, Agent, or Firm—Wegner & Bretschneider

[57] ABSTRACT

Pyridine derivatives of the formula:

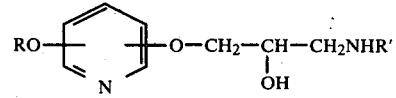

wherein R represents a group $R_1O(CH_2)_2-$, in which $R_1$ is a $(C_{3-6})$cycloalkyl radical, a $(C_{3-6})$cycloalkyl-$(C_{1-4})$alkyl radical or allyl, and R' represents isopropyl or tert.-butyl, are new compounds useful in therapy in the treatment of cardiovascular maladies.

8 Claims, No Drawings

CERTAIN 2,5-DISUBSTITUTED PYRIDINE DERIVATIVES PRODUCING β-ADRENERGIC BLOCKING ACTION

The present invention relates to new therapeutically useful pyridine derivatives, to their preparation and pharmaceutical compositions containing them.

Pyridine derivatives having a β-blocking action have already been described in the literature for example in Ciba-Geigy AG's French Pat. No. 74.05391 (2.218.101). However, the compounds of the present invention differ from the known compounds in their structure and their very good therapeutic action.

The compounds of the present invention are the pyridine derivatives of the general formula:

(I)

RO—[pyridine]—O—CH$_2$—CH(OH)—CH$_2$NHR' wherein R represents a group R$_1$O(CH$_2$)$_2$—, in which R$_1$ is a (C$_{3-6}$) cycloalkyl radical, a (C$_{3-6}$)cycloalkyl-(C$_{1-4}$)alkyl radical or an allyl radical, and R' represents the isopropyl or tert.-butyl radical, and pharmaceutically acceptable acid addition salts thereof.

The pyridine derivatives of this invention contain an asymmetric carbon. The racemates and the laevorotatory and dextrorotatory antipodes form part of the invention.

Preferred compounds are those of general formula I in which the group —O—CH$_2$—CHOH—CH$_2$—NHR' is attached to the 2-position of the pyridine ring and, amongst these, the compounds in which RO— is attached to the 5-position, R and R' being as hereinbefore defined. The radicals represented by symbol R are preferably the 2-[(C$_{3-6}$)cycloalkyl-methoxy]-ethyl and 2-[(C$_{3-6}$)cycloalkyl-oxy]-ethyl radicals.

Compounds presently of outstanding interest are 3-[5-(2-cyclopropylmethoxy-ethoxy)-pyridin-2-yloxy]-1-isopropylamino-propan-2-ol, 3-[5-cyclopentylmethoxy-ethoxy)-pyridin-2-yloxy]-1-isopropylamino-propan-2-ol, 3-[5-(2-cyclohexylmethoxy-ethoxy)-pyridin-2-yloxy]-1-isopropylamino-propan-2-ol, 3-[5-(2-cyclopentyloxyethoxy)-pyridin-2-yloxy]-1-isopropylamino-propan-2-ol, and their pharmaceutically acceptable acid addition salts.

According to the present invention, the pyridine derivatives of general formula (I) are prepared according to several methods:

1. Scheme I

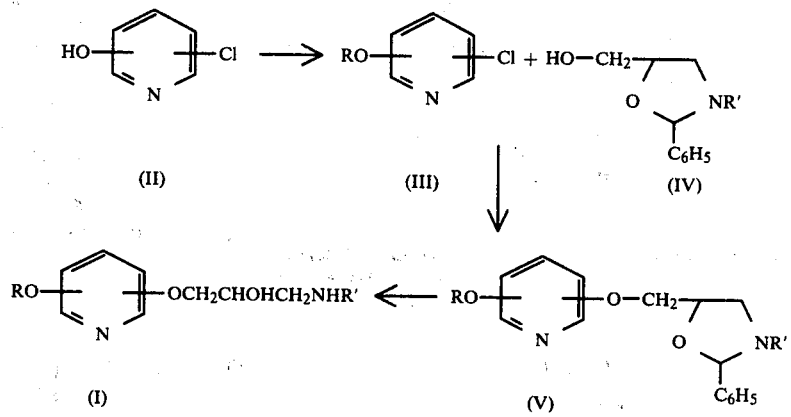

The chloro-hydroxypyridine starting compounds (II) are described in the literature.

The compounds (III) are obtained by reacting a compound (II) with the tosylate of an alcohol ROH (R being as hereinbefore defined) in an organic solvent, such as dimethylformamide (DMF), dimethoxyethane (DME) or diglyme, at a temperature ranging from 20° to 100° C.

The oxazolidines (IV) are known and are described in the literature. They can exist in optically active forms. Consequently, to prepare the optically active compounds (I), a compound (III) can be reacted with an optically active oxazolidine (IV). The reaction of the compound (III) with the oxazolidine (IV) is carried out in an organic solvent, such as dimethylformamide, dimethoxyethane or diglyme, at a temperature of 20° to 150° C.

The oxazolidine ring of the compound (V) is opened in an acid medium at a temperature ranging from 0° to 80° C. to yield a compound (I).

2. Scheme 2

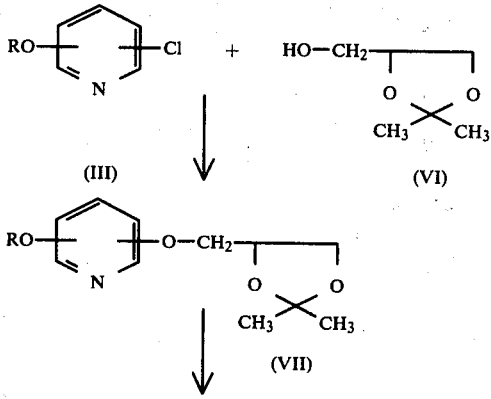

2. Scheme 2
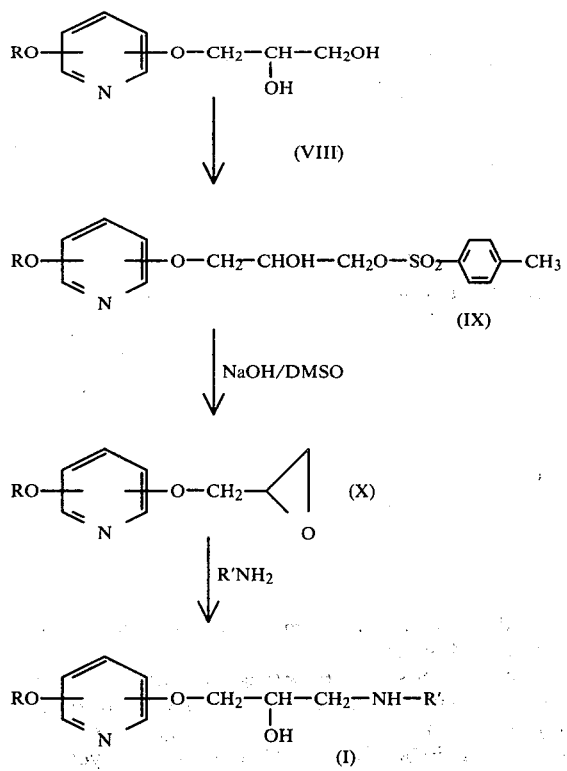
3. Scheme 3
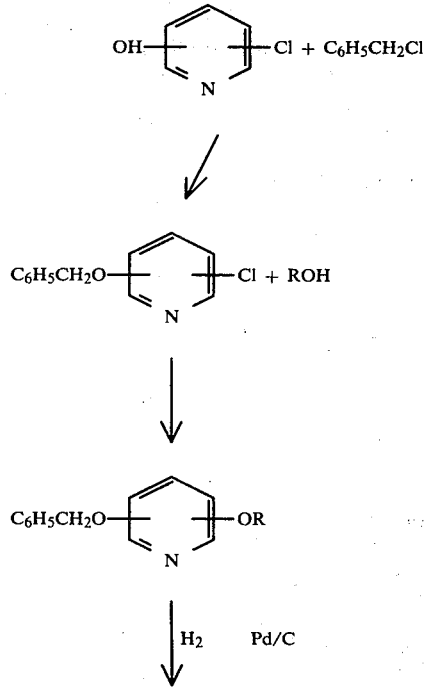
3. Scheme 3 -continued
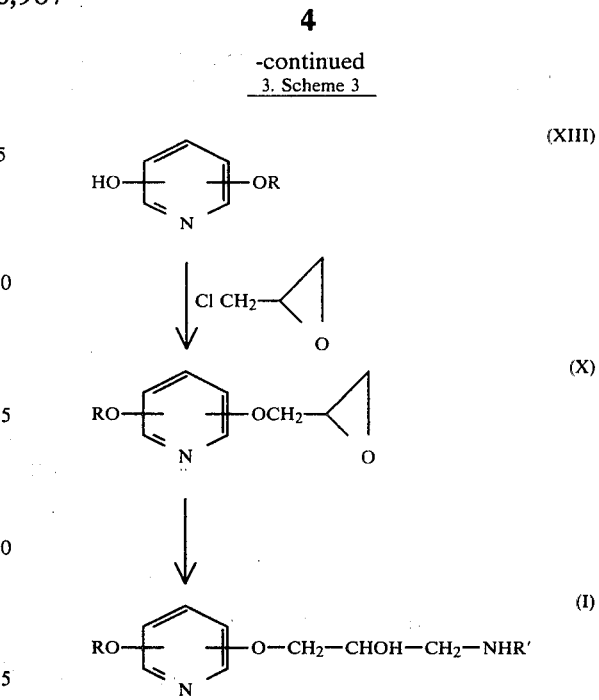
4. Scheme 4 (variant of Scheme 2 starting from a compound VIII)
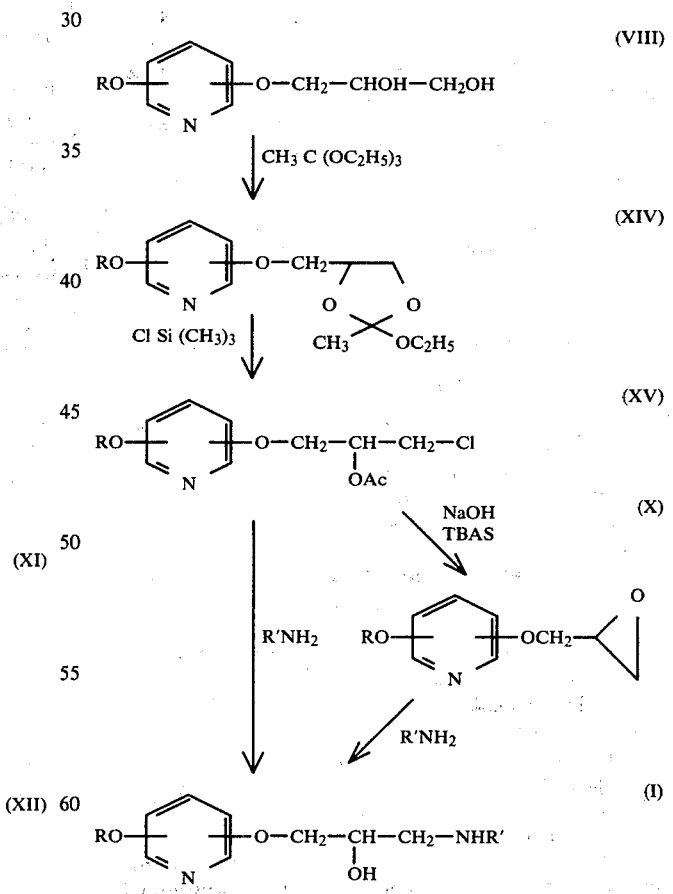
The reaction of the compound (III) with the compound (VI) is carried out in an organic solvent, such as DMF, DME or diglyme, at a temperature ranging from 20° to 150° C.

The opening of the oxazolidine ring of the compound (VII) is carried out in an acid medium at a temperature ranging from 10° to 80° C.

The compound (VIII) is esterified, for example, with the aid of the chloride of a strong organic acid, such as methanesulphonyl or 4-methylphenylsulphonyl chloride. The reaction is carried out in the presence of an inorganic base, for example an alkali metal carbonate or an alkali metal hydroxide or alkaline earth metal hydroxide, or of an organic base such as pyridine or triethylamine, in an organic solvent, such as pyridine or chloroform, and at a temperature from about $-20°$ to $+120°$ C.

The epoxidation can be carried out according to the conventional methods by treating the compound (IX) with an inorganic base, for example an alkali metal hydroxide or alkaline earth metal hydroxide, in a dipolar aprotic solvent, such as DMF, HMPT or DMSO, at a temperature ranging from 20° to 100° C.

It is also possible to obtain the compound of formula (X) by reacting a compound (XIII) with an epihalogenohydrin in the presence of a base, such as an alkali metal hydroxide or hydride, in a suitable organic solvent, such as DMF, DME or diglyme, at a temperature ranging from 20° to 150° C.

It is also possible to obtain the compound (X) by reacting a compound of the formula (VIII) with triethyl orthoacetate and then reacting the product with trimethylsilyl chloride in order to obtain the compound (XIV) and then the compound (XV). The latter gives the epoxide (X) by treatment with a base such as tert.-butylammonium sulphate, in the presence of sodium hydroxide in a chlorinated solvent such as methylene chloride.

By reaction with the amines $R'NH_2$ ($R'$ being as hereinbefore defined) at a temperature from 20° to 150° C., with or without a solvent, the compounds (X) or (XV) give the desired pyridine compounds (I).

Pharmaceutically acceptable acid addition salts of the pyridine derivatives of general formula I can be obtained by methods known per se, for example by reacting the pyridine compound with an acid, the anion of which is relatively innocuous to the animal organism in therapeutic doses of the salts, e.g. fumaric or maleic acid.

The following Examples illustrate the preparation of pyridine derivatives of the present invention. The IR and NMR spectra and the analyses confirmed the structure of the compounds.

EXAMPLE 1

3-[5-(2-Cyclopropylmethoxy-ethoxy)pyridin-2-yl-oxy]-1-isopropylamino-propan-2-ol and its neutral fumarate.

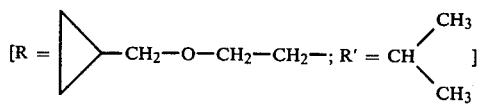

1. 2-Chloro-5-(2-cyclopropylmethoxy-ethoxy)pyridine

A solution of 12.9 g (0.1 mol) of 2-chloro-5-hydroxypyridine in 50 cc of dry dimethylformamide is added to a suspension of 4.8 g (0.1 mol) of sodium hydride (a 50% dispersion in mineral oil) in 200 cc of dimethylformamide. When the evolution of hydrogen has ceased, a solution of 27 g (0.1 mol) of 2-cyclopropylmethoxy-ethanol tosylate in 50 cc of dimethylformamide is added and the mixture is heated at 50°–60° C. for 5 hours. It is then cooled and poured into water; extraction is carried out with diethyl ether and the organic phase is washed with water. After drying, filtration and evaporation of the ether phase, an oil is obtained, which is distilled. Its boiling point (0.1 mm Hg) is 136° C.

2. 3-[5-(2-Cyclopropylmethoxy-ethoxy)pyridin-2-yl-oxy]-1-isopropylamino-propan-2-ol A solution of 6.6 g ($3 \times 10^{-2}$ mols) of 5-hydroxymethyl-3-isopropyl-2-phenyloxazolidine in 10 cc of diglyme is added to a suspension of 1.5 g of sodium hydride (a 50% dispersion in mineral oil) in 50 cc of diglyme. The mixture is heated at 60°–70° C. in order to complete the formation of the sodium derivative, and then cooled with the aid of a bath of iced water. A solution of 6.9 g ($3 \times 10^{-2}$ mols) of 2-chloro-5-(2-cyclopropylmethoxy-ethoxy)pyridine in 10 cc of diglyme is then added and the mixture is heated at a temperature of 140° C. for 3 to 4 hours.

The mixture is cooled and then poured into water, and extraction is carried out with diethyl ether. The ether phase is washed with water, dried over $MgSO_4$ and filtered; the filtrate is evaporated.

The oily residue is taken up in 100 cc of water, 20 cc of concentrated HCl are added and the solution is stirred for 30 minutes at ambient temperature. The benzaldehyde formed is extracted several times with diethyl ether, the aqueous phase is then rendered alkaline with sodium hydroxide solution and extraction is carried out again with diethyl ether. The organic phase is washed with water, dried and evaporated. This yields an oil from which the neutral fumarate of 3-[5-(2-cyclopropylmethoxy-ethoxy)pyridine-2-yl-oxy]-1-isopropylamino-propan-2-ol is prepared in an acetone/diethyl ether mixture. The melting point of the fumarate is 101°–102° C.

EXAMPLE 2

3-[2-(2-Cyclopropylmethoxy-ethoxy)pyridin-5-yl-oxy]-1-isopropylamino-propan-2-ol and its neutral fumarate.

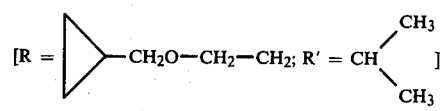

1. 2-Chloro-5-benzyloxypyridine

A solution of 12.9 g (0.1 mol) of 5-hydroxy-2-chloropyridine in 50 ml of dimethylformamide is added to a suspension of 4.8 g (0.1 mol) of sodium hydride (a 50% dispersion in mineral oil; washed with toluene) in 100 ml of dimethylformamide. The mixture is stirred until the evolution of hydrogen has ceased and then, after cooling with the aid of an ice-bath, 12.6 g (0.1 mol, 11.5 cc) of benzyl chloride are introduced dropwise. The mixture is heated at 60° C. for one hour, left to stand overnight and then poured into iced water, and extraction is carried out with diethyl ether. The ether phase is washed with water, dried and filtered and the filtrate is evaporated. The product, i.e. 2-chloro-5-benzyloxypyridine, is distilled. Its boiling point (0.1 mm Hg) is 135° C.

2.
2-(2-Cyclopropylmethoxy-ethoxy)-5-benzyloxypyridine 8.7 g (0.075 mol) of 2-cyclopropylmethoxy-ethanol in 25 cc of diglyme are added to a suspension of 3.6 g (0.075 mol) of sodium hydride (a 50% dispersion in mineral oil; washed with toluene). The mixture is heated at 60°–70° C. in order to complete the formation of the sodium derivative, and then cooled with an ice-bath. A solution of 16.4 g (0.075 mol) of benzyl chloride in 50 cc of diglyme is added dropwise and the mixture is heated to 100° C.

The temperature of the mixture is raised to 130°–140° C. and kept there for 5 hours. Afterwards the mixture is cooled and poured into iced water. Extraction is carried out several times with diethyl ether. The organic extracts are combined, washed with water, dried and filtered and the filtrate is evaporated. The product (identified above) is distilled. Its boiling point (0.1 mm Hg) is 180°–190° C.

3.
2-(2-Cyclopropylmethoxy-ethoxy)-5-hydroxypyridine

A solution of 10 g (0.033 mol) of the obtained product in 100 cc of methanol and 1.9 cc of acetic acid is hydrogenated in a Parr apparatus at ambient temperature, under a hydrogen pressure of 50 psi, in the presence of palladium-on-charcoal as catalyst. When the absorption of hydrogen has ended, the catalyst is filtered off and the filtrate is evaporated. The evaporation residue is taken up in water, the solution is rendered alkaline with sodium hydroxide solution and extraction is carried out with diethyl ether.

The ether phase is washed with water, dried and filtered and the filtrate is evaporated. An oil is collected.

4.
2-(2-Cyclopropylmethoxy-ethoxy)-5-(oxiran-2-yl-methoxy)pyridine 4.2 g ($2 \times 10^{-2}$ mol) of the pyridinol product thus obtained, 5 g of potassium carbonate, 15 ml of oxiran-2-ylmethyl chloride and 50 ml of acetonitrile (CH$_3$CN) are heated under reflux for 12 hours. The mixture is evaporated to dryness and the evaporation residue is taken up in a water/diethyl ether mixture. The ether phase is washed with water, dried with MgSO$_4$ and filtered and the filtrate is evaporated. This yields a yellow oil (the epoxy product named above), which is used without further purification.

5.
3-[2-(2-Cyclopropylmethoxy-ethoxy)pyridin-5-yl-oxy]-1-isopropylamino-propan-2-ol and its neutral fumarate A solution of 5 g of the epoxide product in 50 cc of isopropylamine is heated to the reflux temperature. Reflux is maintained for 24 hours and the mixture is then evaporated to dryness. The residual oil is chromatographed on a silica column (20 g/g, eluant: chloroform/methanol, 95/5).

After evaporation of the pure fractions, the residual oil is triturated in diisopropyl ether and the insoluble material is filtered off. The filtrate is evaporated to dryness and 3.1 g of an oil are collected, from which the fumarate of 3-[2-(2-cyclopropylmethoxy-ethoxy)pyridin-5-yl-oxy]-1-isopropylamino-propan-2-ol is prepared in acetone. The fumarate is recrystallised from acetone; its melting point is 106°–108° C.

EXAMPLE 3

(S)(−)-3-[5-(2-Cyclopropylmethoxy-ethoxy)pyridin-2-yl-oxy]-1-t-butylamino-propan-2-ol and its maleate.

A solution of 3.5 g (0.01 mol) of (S)-2-phenyl-3-t-butyl-5-hydroxymethyloxazolidine in 10 cc of diglyme is added to a suspension of 0.7 g (0.015 mol) of sodium hydride (as a 50% dispersion in mineral oil) in 10 cc of diglyme, and 3.4 g (0.015 mol) of 5-(2-cyclopropylmethoxy-ethoxy)-2-chloropyridine are then added dropwise. The mixture is heated at 130°–140° C. for 6 hours, then cooled and poured into water; extraction of the product is carried out with diethyl ether. The ether phase is washed with water, dried (MgSO$_4$) and filtered and the filtrate is evaporated. This yields an oil of which the maleate of the product named above, recrystallised from acetone, melts at 164°–165° C.

$[\alpha]_D = -10.7$ (c = 1.1, CH$_3$OH).

The following Table shows the compounds of the invention which were prepared by way of Examples.

TABLE

RO—[pyridine ring with N]—O—CH$_2$—CH(OH)—CH$_2$—NHR′

| Compound | Position of OR | Radical R | Position of the group O...NHR′ | R′ | Melting point (°C.) |
|---|---|---|---|---|---|
| 1 racemate | 5 | ▷—CH$_2$O—CH$_2$—CH$_2$— | 2 | —CH(CH$_3$)$_2$ | 101–102 fumarate |
| 1 isomer(s) | | | 2 | " | 115–117 maleate |
| 2 racemate | 5 | ▷—CH$_2$O—CH$_2$—CH$_2$— | 2 | —C(CH$_3$)$_3$ | 168–169 fumarate |
| 2 isomer(s) | | " | | " | 164–165 maleate |

TABLE-continued $$RO-\underset{N}{\underset{|}{\bigcirc}}-O-CH_2-\underset{\underset{OH}{|}}{CH}-CH_2-NHR'$$

| Compound | Position of OR | Radical R | Position of the group O...NHR' | R' | Melting point (°C.) |
|---|---|---|---|---|---|
| 3 | 5 | ⟨▱⟩—CH₂O—CH₂—CH₂ | 2 | —CH(CH₃)₂ | 117–118 fumarate |
| 4 | 5 | ⟨cyclopentyl⟩—CH₂O—CH₂—CH₂— | 2 | —CH(CH₃)₂ | 116–117 fumarate |
| 5 | 5 | ⟨cyclohexyl⟩—CH₂O—CH₂—CH₂ | 2 | —CH(CH₃)₂ | 123 fumarate |
| 6 | 5 | ⟨cyclopentyl⟩—O—CH₂—CH₂— | 2 | —CH(CH₃)₂ | 120–122 fumarate |
| 7 | 5 | ⟨cyclohexyl⟩—O—CH₂—CH₂— | 2 | —CH(CH₃)₂ | 120–121 fumarate |
| 8 | 5 | CH₂=CH—CH₂—O—CH₂—CH₂— | 2 | —CH(CH₃)₂ | 102–103 fumarate |
| 9 | 2 | ⟨cyclopropyl⟩—CH₂O—CH₂—CH₂— | 5 | —CH(CH₃)₂ | 106–108 fumarate |

The compounds of general formula I of the present invention were subjected to a series of pharmacological tests which demonstrated their advantageous properties in the cardiovascular field.

The acute toxicity on oral and intravenous administration was evaluated on male mice of the CD1 strain, having an average weight of 20 g. The mortality was noted over a 5-day period following the administration of the compounds. The 50% lethal dose (LD 50) was calculated according to Litchfield and Wilcoxon (J. Pharmacol. Exp. Ther., 1944, 95, 99). The LD 50 ranges from 600 to 2000 mg/kg animal body weight, administered orally.

Studies on isolated organs: Isolated auricles were used, which had been taken from rats weighing 250 to 350 g and had been kept in oxygenated Moran's solution (in g/liter: NaCl=7.02; KCl=0.42; CaCl₂=0.24; MgCl₂=0.20; NaHCO₃=2.0; glucose=1.8) (95% of O₂; 5% of CO₂) at a temperature of 31° C. The tachycardia was studied, together with the increase in the contractile force caused by isoprenaline (curve of dose/response to the agonist), before and after the addition of the antogonist (compound of general formula I or reference substance), and the pA₂ of each of them was calculated by the method of Arunlakshana and Schild (Brit. J. Pharmacol. 1959, 14, 48), the pA₂ representing the logarithm of the molar concentration of competitive antagonist requiring twice as strong a dose of agonist to cause the same responses as those obtained in the absence of antagonist. The pA₂ of the compounds is between 8 and 9.

All the compounds of general formula I possess an inhibiting action against the cardiac effects of isoprenaline, but not against the hypotensive effects of the latter; therefore, they are indeed selective blocking agents for the β₁-adrenergic receptors, that is to say the β-adrenergic receptors located in the heart, and not the β₂-adrenergic receptors located in the vessels. The above results show that the compounds of this invention can be used in human and veterinary medicine in cardiovascular diseases and, in particular, in coronary complaints, complaints affecting the myocardium, and cardiac rhythm disorders.

The present invention consequently includes within its scope all pharmaceutical compositions which contain a compound of general formula I, or an acid addition salt thereof, as active principle, in association with any excipients suitable for their oral, rectal or parenteral administration. These pharmaceutical compositions can also contain other medicinal substances with which these compounds and their acid addition salts are pharmaceutically and therapeutically compatible.

For oral administration, all the pharmaceutical forms suitable for this method can be used, that is to say tablets, coated tablets, pills, capsules, cachets, and solutions and suspensions to be taken orally, the individual portion of the active principle in such administered compositions varying between 5 and 100 mg, and the daily dose being between 10 and 300 mg.

For endorectal administration, suppositories are used which contain 10 to 100 mg of active principle and which are administered to the patient at a rate of 1 to 3 per 24 hours.

For parenteral administration, stabilised and buffered injectable solutions are used, which have been prepared in advance or extemporaneously. The dose of active principle per individual portion can vary between 1 and 10 mg and the daily dose is between 3 and 50 mg.

We claim:

1. A compound of the formula:

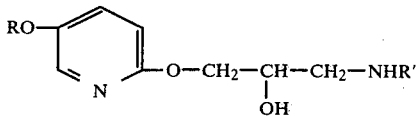

wherein R represents a group $R_1O(CH_2)_2$— in which $R_1$ is a $(C_{3-6})$cycloalkyl radical, or a $(C_{3-6})$cycloalkyl-$(C_{1-4})$alkyl radical, and R' represents isopropyl or tert.-butyl, and its pharmaceutically acceptable acid addition salts.

2. A compound according to claim 1 wherein R represents a 2-[$(C_{3-6})$cycloalkyl-methoxy]-ethyl or 2-[$(C_{3-6})$cycloalkyl-oxy]-ethyl radical.

3. A compound according to claim 1 which is 3-[5-(2-cyclopropylmethoxy-ethoxy)-pyridin-2-yloxy]-1-isopropylamino-propan-2-ol and its pharmaceutically acceptable acid addition salts.

4. A compound according to claim 1 which is 3-[5-(2-cyclopentylmethoxy-ethoxy)-pyridin-2-yloxy]-1-isopropylamino-propan-2-ol and its pharmaceutically acceptable acid addition salts.

5. A compound according to claim 1 which is 3-[5-(2-cyclohexylmethoxy-ethoxy)-pyridin-2-yloxy]-1-isopropylamino-propan-2-ol and its pharmaceutically acceptable acid addition salts.

6. A compound according to claim 1 which is 3-[5-(2-cyclopentyloxy-ethoxy)-pyridin-2-yloxy]-1-isopropylamino-propan-2-ol and its pharmaceutically acceptable acid addition salts.

7. A pharmaceutical composition for producing selective blocking of beta-adrenergic receptors in the heart which comprises a dose of a compound of the formula depicted in claim 1, or a pharmaceutically acceptable acid addition salt thereof effective for producing such blocking, in assoication with a suitable excipient for incorporation in a pharmaceutical composition.

8. Method for producing beta-adrenergic blocking and correcting cardia rhythm disorders in a patient which comprises administering to said patient an amount of a compound of the formula of claim 1, or a pharmaceutically acceptable acid addition salt thereof, in a dose effective to produce the said effects.

* * * * *